United States Patent
Schuetzle et al.

(10) Patent No.: US 10,478,806 B2
(45) Date of Patent: Nov. 19, 2019

(54) PROCESS AND CATALYST SYSTEM FOR THE PRODUCTION OF HIGH QUALITY SYNGAS FROM LIGHT HYDROCARBONS AND CARBON DIOXIDE

(71) Applicant: CARBON RECYCLING SOLUTIONS, LLC, Sacramento, CA (US)

(72) Inventors: Robert Schuetzle, Sacramento, CA (US); Dennis Schuetzle, Grass Valley, CA (US)

(73) Assignee: Carbon Recycling Solutions, LLC, Sacramento, CA (US)

(*) Notice: Subject to any disclaimer, the term of this patent is extended or adjusted under 35 U.S.C. 154(b) by 0 days.

(21) Appl. No.: 15/530,981

(22) Filed: Mar. 31, 2017

(65) Prior Publication Data

US 2017/0246618 A1     Aug. 31, 2017

Related U.S. Application Data

(63) Continuation of application No. 14/120,973, filed on Jul. 16, 2014, now Pat. No. 9,611,145.

(Continued)

(51) Int. Cl.
*B01J 23/755* (2006.01)
*C01B 3/40* (2006.01)
(Continued)

(52) U.S. Cl.
CPC ............. *B01J 23/755* (2013.01); *C01B 3/40* (2013.01); *C01B 3/48* (2013.01); *C07C 1/22* (2013.01); *C07C 29/153* (2013.01); *C10G 2/332* (2013.01); *C10G 2/333* (2013.01); *C10J 1/20* (2013.01); *C10L 1/08* (2013.01); *C22C 19/07* (2013.01); *B01J 23/78* (2013.01); *C01B 2203/0233* (2013.01); *C01B 2203/0238* (2013.01);
(Continued)

(58) Field of Classification Search
CPC .................................................... B01J 23/755
See application file for complete search history.

(56) References Cited

U.S. PATENT DOCUMENTS 2,546,017 A     3/1951   Schiller et al.
2,693,880 A    11/1954   Schoenfeld
(Continued)

FOREIGN PATENT DOCUMENTS

CN          102935998 A  *  2/2013

OTHER PUBLICATIONS

Wang, T. et al. Fuel Processing Tech. 2006, 87, 421-428 (Year: 2006).*

(Continued)

*Primary Examiner* — Medhanit W Bahta
(74) *Attorney, Agent, or Firm* — Jeffrey A. McKinney; McKinney Law Group APC

(57) ABSTRACT

The present invention describes a process and catalysts for the conversion of a light hydrocarbon and carbon dioxide input stream into high quality syngas with the subsequent conversion of the syngas into fuels or chemicals. In one aspect, the present invention provides an efficient, solid solution catalyst for the production of a carbon containing gas from carbon dioxide and light hydrocarbons. The catalyst comprises a single transition metal, and the transition metal is nickel.

10 Claims, 7 Drawing Sheets

Related U.S. Application Data

(60) Provisional application No. 61/958,235, filed on Jul. 22, 2013.

(51) Int. Cl.

| | | |
|---|---|---|
| *C10G 2/00* | (2006.01) | |
| *C07C 1/22* | (2006.01) | |
| *C10J 1/20* | (2006.01) | |
| *C07C 29/153* | (2006.01) | |
| *C22C 19/07* | (2006.01) | |
| *C10L 1/08* | (2006.01) | |
| *C01B 3/48* | (2006.01) | |
| *B01J 23/78* | (2006.01) | |

(52) U.S. Cl.
CPC ............ *C01B 2203/0244* (2013.01); *C01B 2203/0261* (2013.01); *C01B 2203/0283* (2013.01); *C01B 2203/061* (2013.01); *C01B 2203/062* (2013.01); *C01B 2203/1058* (2013.01); *C01B 2203/1241* (2013.01); *Y02P 20/52* (2015.11); *Y02P 30/30* (2015.11)

(56) References Cited

U.S. PATENT DOCUMENTS

| | | |
|---|---|---|
| 4,495,307 A | 1/1985 | Clements |
| 5,229,347 A | 7/1993 | Prada et al. |
| 6,402,989 B1 | 6/2002 | Gaffney |
| 8,394,862 B1 | 3/2013 | Schuetzle et al. |
| 2003/0162847 A1 | 8/2003 | Harford et al. |
| 2005/0166447 A1 | 8/2005 | Corkwell et al. |
| 2006/0144755 A1 | 7/2006 | Benazzi et al. |
| 2008/0108716 A1 | 5/2008 | Ayasse |
| 2009/0133407 A1 | 5/2009 | Sawyer |
| 2009/0300970 A1 | 12/2009 | Perego |
| 2010/0160463 A1 | 6/2010 | Wang |
| 2011/0027170 A1 | 2/2011 | Lee et al. |
| 2012/0161078 A1* | 6/2012 | Saito ............... B01J 23/002 252/373 |
| 2012/0208902 A1 | 8/2012 | Kresnyak et al. |
| 2013/0022537 A1 | 1/2013 | Brandt et al. |
| 2013/0072583 A1 | 3/2013 | Koskinen et al. |
| 2013/0144098 A1 | 6/2013 | Pansare et al. |

OTHER PUBLICATIONS

CN102935998A, Feb. 2013; English translation (Year: 2013).*
Ruckenstein, et al., "Carbon dioxide reforming of methane over nickel/alkaline earth metal oxide catalysts," Applied Catalysis A: General, pp. 149-161, vol. 133:1 (1995).

* cited by examiner

PROCESS AND CATALYST SYSTEM FOR THE PRODUCTION OF HIGH QUALITY SYNGAS FROM LIGHT HYDROCARBONS AND CARBON DIOXIDE

This application claims is a continuation of U.S. patent application Ser. No. 14/120,973, filed Jul. 16, 2014, entitled "Process and Catalyst System for the Production of Diesel Fuel from Light Hydrocarbons and Carbon Dioxide", which claims priority from U.S. Provisional Patent Appl. No. 61/958,235, filed Jul. 22, 2013, entitled, "Process and Catalyst System for the Production of Diesel Fuel from Light Hydrocarbons and Carbon Dioxide", both of which are incorporated by reference into this application in their entirety.

FIELD OF THE INVENTION

The present invention describes a process and catalysts for the conversion of light hydrocarbons and carbon dioxide input streams into high quality syngas that is used to produce fuels (e.g. diesel fuel) and chemicals.

BACKGROUND OF THE INVENTION

The efficient conversion of light hydrocarbon gases, such as natural gas, and carbon dioxide into high quality syngas has several commercial and financial advantages:

A) Some natural gas or light hydrocarbon resources can't be economically recovered since the local infrastructure is not adequate to economically transport this gas to commercial customers. These resources are typically referred to as "stranded resources".

B) Natural gas resources can contain 2-50% (or higher) carbon dioxide which needs to be removed at the extraction site before commercial use.

C) Natural gas resources contain varying amounts of $C_2$-$C_6$ hydrocarbons which needs to be removed at the extraction site or from the natural gas pipelines before commercial use of the natural gas.

D) Many other processes (e.g. power plants, cement plants, ethanol production, petroleum refining, chemical plants, etc.) produce carbon dioxide which is usually discharged into the atmosphere. Since carbon dioxide has been identified as a significant greenhouse gas, these carbon dioxide emissions need to be reduced from these processes. Although, this carbon dioxide can be used to enhance oil and gas recovery from wells in limited cases, the majority of this captured carbon dioxide will be emitted into the atmosphere. Since carbon dioxide is a carbon containing gas, the preferred method is to efficiently capture the carbon dioxide and convert it to fuels (e.g. diesel fuel) and chemicals.

The conversion of light hydrocarbon gases into more valuable chemical products typically involves syngas generation. Syngas generation involves converting natural gas, which is mostly methane, to syngas, which is primarily a mixture of carbon monoxide and hydrogen. Syngas may be used as a feedstock for producing a wide range of chemical products, including liquid fuels, alcohols, acetic acid, dimethyl ether and many other chemical products. However, this syngas needs to be directly produced and converted at the resource site to fuels and/or chemical products since it is not practical to transport the syngas to distant refineries and chemical processing plants.

There are a few possible approaches to converting remote natural gas assets into syngas. Several catalysts are commercially available to convert natural gas into syngas. The syngas produced has a $H_2$/CO ratio that varies from 3.0-4.5/1.0. However, the $H_2$/CO ratio needs to be in the proper stoichiometric range of 1.5-2.5/1.0 for the production of fuels and chemicals. Unless otherwise stated, syngas ratios (and percentage compositions) as described herein are in terms of molar ratios (and molar percentages).

Since the syngas generation is a potentially costly step, it is important to produce syngas with the desired $H_2$/CO ratio for the subsequent production of the desired products. Therefore, several alternative processes for syngas generation have been developed.

One alternative process for syngas generation involves the catalytic or thermal reforming reaction between carbon dioxide and methane (typically referred to as dry reforming). An attractive feature of this method is that carbon dioxide is converted into syngas; however, this method has problems with rapid carbon deposition. The carbon deposition or coke forming reaction is a separate reaction from the one that generates the syngas and occurs subsequent to the syngas formation reaction. However, the reaction of methane in dry reforming is slow enough that long residence times are required for high conversion rates and these long residence times lead to coke formation. The ratio of hydrogen to carbon monoxide, which is formed from this process, is typically approximately 1.0.

A second alternative process for synthesis gas generation involves partial oxidation of methane using oxygen, where the oxygen can be either air, enriched air, or oxygen with a purity in excess of 90%, preferably in excess of 99%. The ratio of hydrogen to carbon monoxide, which is formed from this process, is typically approximately 2.0. However, in commercial practice, some amount of steam is typically added to a partial oxidation reformer in order to control carbon formation and the addition of steam tends to increase the $H_2$/CO ratio above 2.0. Likewise it is common to add relatively small amounts of $CO_2$ to the feed gas mixture in an attempt to adjust the ratio closer to 2.0.

A third approach is to produce syngas with a $H_2$/CO ratio between 0.5 and 1 using a mixture of LPG and $CO_2$ (Calcor process). See, *Hydrocarbon Processing*, Vol. 64, May 1985, pp. 106-107 and "A new process to make Oxo-feed," Hydrocarbon Processing, Vol. 66, July 1987, pg. 52. However, many natural gas resource sites, in particular the stranded natural gas sites, do not have the infrastructure available to separate LPG and $CO_2$ from the natural gas.

Many processes and catalyst formulations have been reported in the literature for the reforming of light hydrocarbon gases or carbon dioxide. In the first step in the process, the production of syngas traditional catalysts do not meet the following criteria: 1) exhibits high thermal stability up to 1,100° C.; 2) does not produce elemental carbon (coking); 3) has good resistance to contaminants that may be present in captured $CO_2$ and natural gas streams; 4) can be reduced in-situ in the catalytic reactor; 5) exhibits good physical hardness and will not physically degrade over time; 6) will efficiently co-convert $CH_4$ and $CO_2$, with and without the presence of water.

It is possible to produce syngas with a $H_2$/CO ratio that is above the ratio ideally desired for the process in which the syngas is to be used, and then to remove excess hydrogen to adjust the ratio to the desired value. However, the $H_2$ removal process employs expensive $H_2$ separation systems that tend to foul and decline in performance with use.

Some natural gas extraction plants produce LPG as well as the natural gas. The export of LPG from such a facility or from the parent natural gas field is often difficult and expensive. The LPG must be compressed or liquefied, and the shipment requires the use of special transportation vessels. Furthermore, the market for mixtures of propane and butane is limited and of reduced value. Thus, the LPG must be separated into individual propane and butane of sufficient purity to meet commercial specifications. This complicated and expensive operation often results in high costs, which limits the value of the LPG at the production site.

The conversion of natural gas to liquid fuels further involves the production of some quantities of greenhouse gas emissions, such as $CO_2$, which is environmentally undesirable.

Following the production of the synthesis gas, many processes and catalysts have been proposed for the production of transportation fuels and chemicals. However, the traditional process for production of fuels and chemicals from syngas involves the production first of a paraffinic wax product that is then refined into fuels and/or chemicals. The refining step is capital intensive and complex to operate, therefore requiring large plant sizes to justify this refining system.

Accordingly, there is a need for a process for producing a syngas with a pre-selected $H_2/CO$ ratio that can be varied according to the process in which the syngas is to be employed and that avoids $H_2$ separation and coking in the syngas formation step. There is also a need for a process that minimizes or eliminates production of LPG from a processing facility, such as, for example, a hydrocarbon synthesis facility. Furthermore, there is a need to reduce the greenhouse emissions from a processing facility, such as, for example, an on-site fuel production plant. In addition, the need to directly produce a usable diesel fuel without having to refine a hydrocarbon wax is required to justify lower plant capital and operating costs.

SUMMARY OF THE INVENTION

Figure 1:
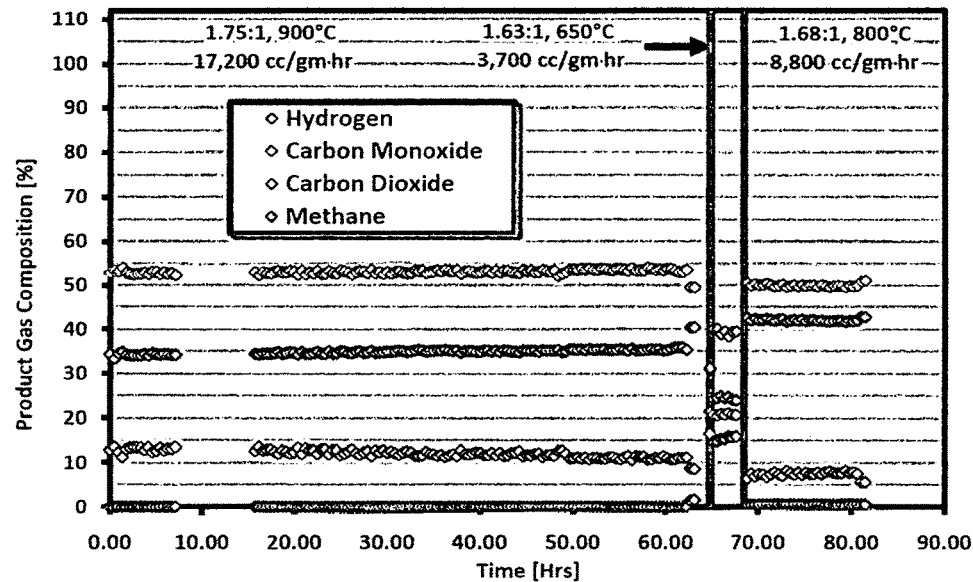
FIG. 1 shows a graph related to the ability of a catalyst to dry reform mixtures of $CO_2$ and $CH_4$.

The present invention relates to a process whereby a mixture of light hydrocarbons and carbon dioxide is catalytically converted into a high-quality syngas which can then be used to produce diesel fuel grade liquid hydrocarbon and/or other valuable higher hydrocarbon steams, whereby the carbon dioxide steam is generated by separation from a flue gas stream or by other means or exists as part of the natural gas stream. The light hydrocarbons and carbon dioxide are supplied to a first reactor that utilizes a first catalyst whereby the light hydrocarbons and carbon dioxide are converted into high quality syngas. The syngas output of the first reactor is connected as an input to a second reactor that utilizes a second catalyst to form a diesel fuel grade liquid hydrocarbon and other hydrocarbon byproducts.

The first catalyst used in the process is a high-performance solid solution Ni-based catalyst that is highly versatile, and which efficiently produces high-quality syngas under dry reforming ($CH_4$ and $CO_2$), combination dry/steam reforming ($CH_4$, $CO_2$ & $H_2O$), or tri-reforming ($CH_4$, $CO_2$, $H_2O$ & $O_2$) conditions. The robust, solid solution Ni-based catalysts have high thermal stability up to 1,100° C., do not form carbon (coking), and have good resistance to contaminants that may be present in captured $CO_2$ streams, natural gas, biogas or other gas feedstock sources.

The first catalyst is also capable of reforming complex and higher molecular weight hydrocarbons without coking or other deactivation that occurs on traditional steam methane reforming (SMR) and other reforming catalyst systems. This catalyst exhibits high activity at low Ni concentrations (5-20 wt. %), compared to other catalysts that require at least 30 wt. % Ni. Furthermore, the use of expensive precious metals to enhance catalyst performance is not necessary. High conversion efficiencies of light hydrocarbons in the feed stream of 90-100% are achieved when the catalyst is operated under the recommended space velocities and temperature conditions outlined in this invention.

The second catalyst contains from about 2 to about 50 parts-by-weight cobalt and from about 0.1 to about 20 parts-by-weight of at least one metal selected from a group consisting of cerium, ruthenium, lanthanum, platinum, or rhenium per 100 parts-by-weight of a support selected from a group consisting of silica, alumina, and combinations thereof.

The carbon dioxide supplied as an input to the process is either contained within the natural gas stream or is obtained by separating the carbon dioxide from a flue gas stream exiting the first reactor, whereby an alkylamine is used to remove the carbon dioxide from the flue gas steam. Alkylamines used in the process include monoethanolamine, diethanolamine, methydiethanolamine, disopropylamine, aminoethoxyethnol, or combinations thereof.

DETAILED DESCRIPTION OF THE INVENTION

The present invention describes a process and catalysts for the conversion of a light hydrocarbon and carbon dioxide input stream into a diesel fuel grade liquid hydrocarbon usable as a compression ignition fuel which may contain a majority of C8-C24 paraffins.

The invention utilizes a first reactor system whereby light hydrocarbons which may include but are not limited to natural gas, naphtha, natural gas liquids, bio-gas containing methane, or other similar gases are blended with carbon dioxide and optionally steam, oxygen, or oxygen containing gases such as air.

The first reactor system utilizes a first catalyst that is a robust, Ni based solid-solution catalyst that reforms the feed gases into a carbon containing output gas.

In comparison to other catalysts developed for this application, this first solid-solution catalyst utilizes only one transition metal, Ni, whereas all other reforming catalysts employ two or more transition metals. See, U.S. Pat. Nos. 6,423,665, 7,432,222, WO 2000/016899, and U.S. Pat. Pub. No. 0314993. Several other prior art formulations require the use of expensive precious metals (e.g. Pt, Pd, Rh, Ru and Ir). See, U.S. Pat. Nos. 6,409,940 and 5,431,855.

Other formulations require that the active catalyst material needs to be coated on catalyst substrates (e.g. $Al_2O_3$). Moreover, this is the only solid-state catalyst formulation that is versatile and is able to produce high-quality carbon containing product gas under dry reforming ($CH_4$ and $CO_2$), combination dry/steam reforming ($CH_4$, $CO_2$ & $H_2O$), or tri-reforming ($CH_4$, $CO_2$, $H_2O$ & $O_2$) conditions.

The carbon containing product gas is then fed into a second reactor system that utilizes a second catalyst that contains from about 2 to about 50 parts-by-weight cobalt and from about 0.1 to about 20 parts-by-weight of at least one metal selected from a group consisting of cerium, ruthenium, lanthanum, platinum, or rhenium per 100 parts-by-weight of a support selected from a group consisting of silica, alumina, and combinations thereof.

The integrated process above requires a carbon dioxide input. In one embodiment, the carbon dioxide is supplied from the separation of the carbon dioxide in the flue gas stream exiting the first reactor, and the separation is done using an alkylamine.

Alkylamines used in the process can include monoethanolamine, diethanolamine, methyldiethanolamine, disopropylamine, aminoethoxyethnol, or combinations thereof. In another embodiment, the carbon dioxide is already contained in the natural gas feedstock.

In another embodiment, the carbon dioxide exists as part of the natural gas or natural gas liquids stream.

The manufacturing process for the first catalyst is important as well in that it produces a catalyst that forms a unique solid solution phase, bi-metallic crystalline phase that leads to no segregation of the metal phases. This unique chemical structure leads to enhanced resistance to coking, when compared to conventional metal supported reforming catalysts. This also leads to enhanced resistance to syngas poisons such as sulfur and ammonia. In addition, this catalyst has enhanced catalytic activity at lower surface area compared to monometallic segregated catalyst phase for example Ni on alumina. This catalyst requires no alkali promotion needed to curb the carbon deposition typically seen with feed gases as described herein. The catalyst is operable in a variety of dry, steam, combined dry/steam and tri-reforming feeds. Mixes of higher hydrocarbon feedstocks are also achievable with this catalyst.

The first catalyst manufacturing may involve some or all of the following steps that will achieve a commercial solid solution catalyst: A) mixing of $Ni_2O$ powders at the 5-15 wt. % level with one or more alkali metal oxides (e.g. MgO, CaO); B) fusing of these oxide mixtures at temperatures in the range of 900-1,100° C. for 4-12 hours; C) calcining the catalyst the first time; D) grinding of the fused mixtures to produce the proper catalyst size, typically in the 500-3,000 um range; E) calcining the catalyst the second time.

EXAMPLES

A variety of tests were conducted on the first catalyst including dry reforming ($CO_2$ and $CH_4$), combination dry/steam reforming ($CO_2$, $CH_4$ & $H_2O$), and tri-reforming ($CO_2$, $CH_4$, $H_2O$ & $O_2$). $CH_4$ and $CO_2$ conversions averaged up to 95-100% at the optimum temperatures and gas space velocities. No formation of carbon deposits (coking) on the catalyst was observed in any of these tests. The following sections provide examples that support the superior performance of these catalysts over currently available technologies.

Dry Reforming—In Dry (or $CO_2$) Reforming, methane and carbon dioxide are reacted and produce a syngas with low $H_2$/CO ratio of 0.7-1.0:

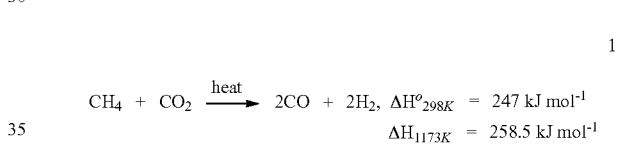

Steam Reforming—Steam Methane Reforming (SMR) is an endothermic process where methane is reacted with steam at high temperatures to produce a syngas with a high $H_2$/CO ratio:

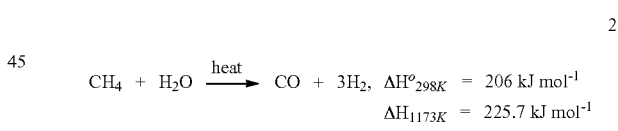

Partial Oxidation—Reactions for the exothermic oxidation of methane are shown below:

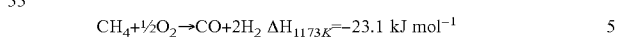

Water-Gas-Shift Equilibrium—The Water-Gas Shift (WGS) equilibrium reaction, equation 6, also occurs during reforming and will adjust the final syngas product ratio depending on how the equilibrium is influenced. If, for instance, dry reforming is conducted in an excess of $CO_2$, then the reverse WGS will be favored which will increase the CO content and produce water. Likewise, excess steam in the SMR reaction will tend to drive the forward water gas shift resulting in higher $H_2$ and some $CO_2$ products.

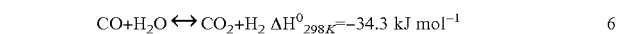

Reactions for Coke Formation and Destruction—The desired reforming reactions above are often accompanied by side or intermediate reactions that involve elemental carbon (or coke). The equations below show some of the ways that carbon can be formed and reformed from the reactants and products. One possible pathway to the desired products of CO and $H_2$ is methane decomposition on the catalyst (Eq. 7) and or carbon monoxide disproportionation (Eq. 8) followed by carbon reforming (Eq. 9-11). However, it is the buildup of elemental carbon in reactors that is one of the main factors of catalyst lifetime and much research is focused on limiting its formation. Catalysts were analyzed for carbon formation during test runs.

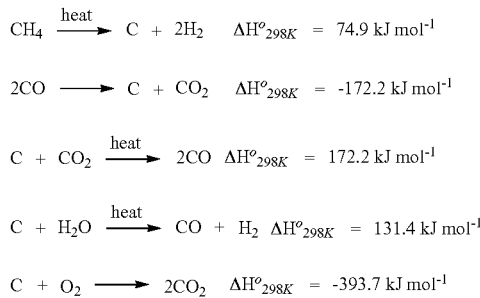

$$CH_4 \xrightarrow{heat} C + 2H_2 \quad \Delta H°_{298K} = 74.9 \text{ kJ mol}^{-1} \quad (7)$$

$$2CO \longrightarrow C + CO_2 \quad \Delta H°_{298K} = -172.2 \text{ kJ mol}^{-1} \quad (8)$$

$$C + CO_2 \xrightarrow{heat} 2CO \quad \Delta H°_{298K} = 172.2 \text{ kJ mol}^{-1} \quad (9)$$

$$C + H_2O \xrightarrow{heat} CO + H_2 \quad \Delta H°_{298K} = 131.4 \text{ kJ mol}^{-1} \quad (10)$$

$$C + O_2 \longrightarrow 2CO_2 \quad \Delta H°_{298K} = -393.7 \text{ kJ mol}^{-1} \quad (11)$$

As discussed above, this catalyst performed well under mixed reforming conditions and was selected based on several reasons. First, the catalyst shows high thermal stability and negligible carbon formation under a variety of target reforming conditions including dry reforming, which is typically a challenge for other reforming catalysts. Another benefit of the catalyst is that the base material has high thermal stability and shock resistance, both of which are important for commercial plants. Also, the catalyst provides acceptable commercial costs as well as good conversion efficiencies and stability over time. In addition, another benefit is that this catalyst performs well in the reformation of the small percentage of higher hydrocarbons that are in the feed stream from both natural gas and other feed streams. Experimental results on the catalyst for tri-reforming, dry-reforming, and combination reforming are summarized below.

Example #1

In this example, the ability of the catalyst to dry reform mixtures of $CO_2$ and $CH_4$ are described. Dry reforming tests were initiated at 1.75/1.0 $CO_2/CH_4$ and 900° C. (Run A). The results are shown in FIG. 1. The ratio of $CO_2/CH_4$ changed slightly as the space velocity was altered due to insufficient calibration of the flow meters. This problem was discovered during data analysis and was corrected in later runs. At 900° C., full methane conversion was achieved, and the sample operated without loss of activity or pressure increase. At 650° C., the methane conversion was low. The catalyst achieved 95% methane conversion at 800° C. and demonstrated stable performance without pressure increase.

Figure 2:
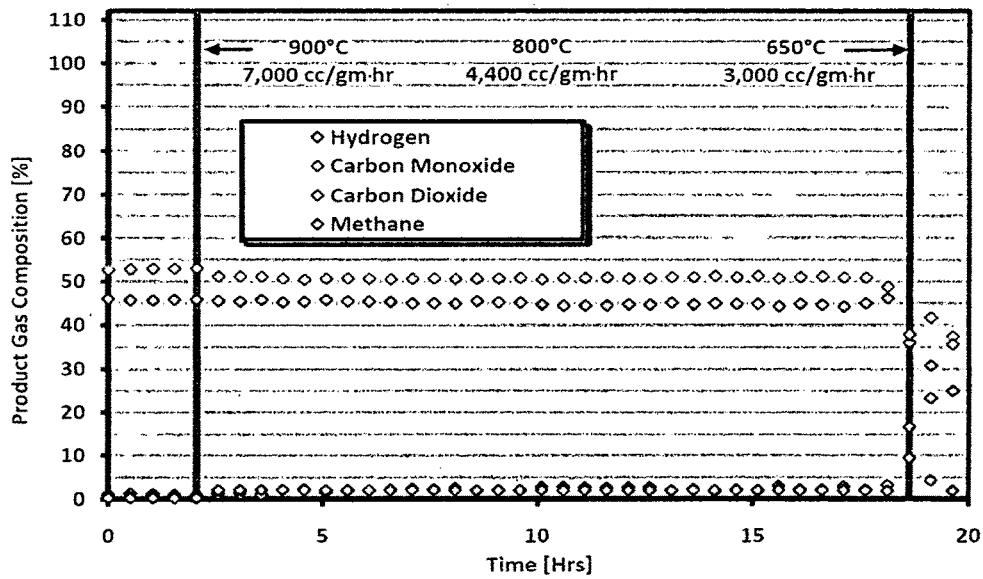
FIG. 2 shows a graph related to the performance of a catalyst with a $CO_2/CH_4$ (1.1/1.0) feed.

In the next set of tests, the performance of the catalyst under more challenging conditions was examined (see FIG. 2). The performance of the catalyst with a $CO_2/CH_4$ (1.1/1.0) feed was carried out. At 900° C., the complete conversion of methane and carbon dioxide was observed over the first several hours, and complete conversion continued overnight at 800° C. for 18 hours. There was no loss in performance at the higher temperatures, although the pressure drop through the reactor increased from 2 psi to about 4 psi overnight.

The catalyst was tested at 650° C. the following day, but immediate loss in performance and reactor blockage quickly ensued. Analysis of the sample, as discussed in the following section, confirmed that the catalyst coked (produced carbon that plugged the reactor). This is typical for reforming catalysts at lower temperatures under dry reforming conditions and the catalyst performed well, without carbon deposition, at $CO_2/CH_4$ ratios greater than 1.5/1.0 and temperatures greater than 800° C.

Figure 3:
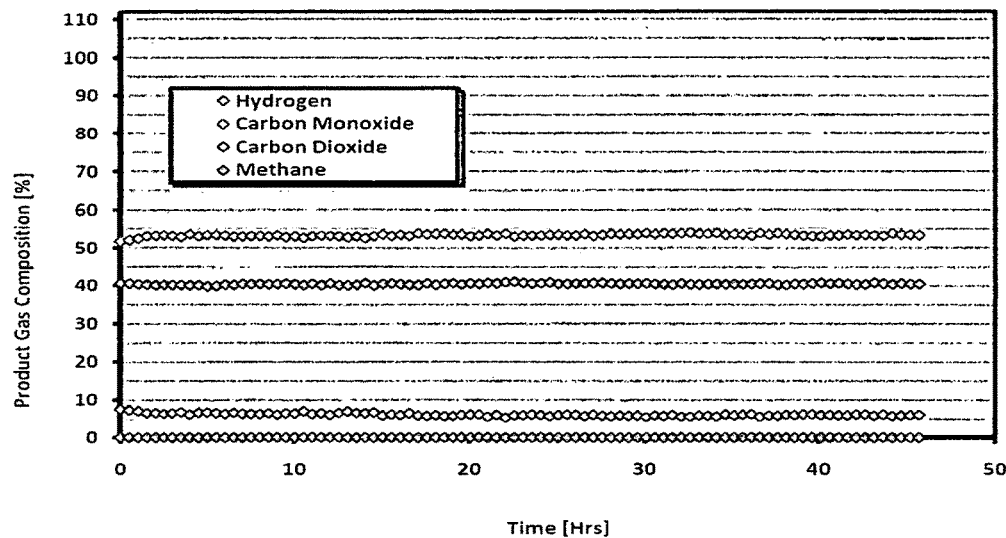
FIG. 3 shows a graph related to a dry reforming test run at an intermediate ratio of $CO_2/CH_4$ (1.5/1.0).

Finally, a dry reforming test was run (Test C) at an intermediate ratio of $CO_2/CH_4$ (1.5/1.0) as shown in FIG. 3. At 900° C., the catalyst was stable for 2 days of operation before the run was terminated to analyze the catalyst for carbon. The pressure didn't increase during the test, and the activity did not change.

Dry reforming, under all of the conditions described above, produces a syngas with a $H_2/CO<1.0$ that is not entirely suitable for subsequent conversion to diesel fuel. However, if a source of external renewable hydrogen was available or if hydrogen already exists in the flue gas stream from a stationary emissions source (for example in IGCC power plants), then dry reforming is an attractive option for use in this catalytic system which provides high $CO_2$ conversion efficiencies and a methane to carbon dioxide input ratio that provides very attractive commercial economics (since the feed gas can contain up to ~70% $CO_2$).

Example #2

The ability of the catalyst to carry out a combination of dry and steam reforming of $CO_2$, $CH_4$ & $H_2O$ is summarized in this example. Combination dry reforming/steam methane reforming tests includes $CO_2$, $CH_4$ and $H_2O$ reactants in various molar ratios. In addition to the dry reforming reactions, Steam Methane Reforming (SMR) also occurs and is an endothermic process where methane reacts with steam at high temperatures to produce syngas.

By combining dry and steam reforming, a syngas with an ideal $H_2/CO$ can be produced. Mixed steam and dry methane reforming tests were conducted to demonstrate activity and determine product composition with methane, $CO_2$, and steam in the feed. In the first test, the reforming mixture was run with the following gas composition: $CO_2/CH_4/H_2O$ (0.9/1.0/2.2) at 900° C.

Figure 4:
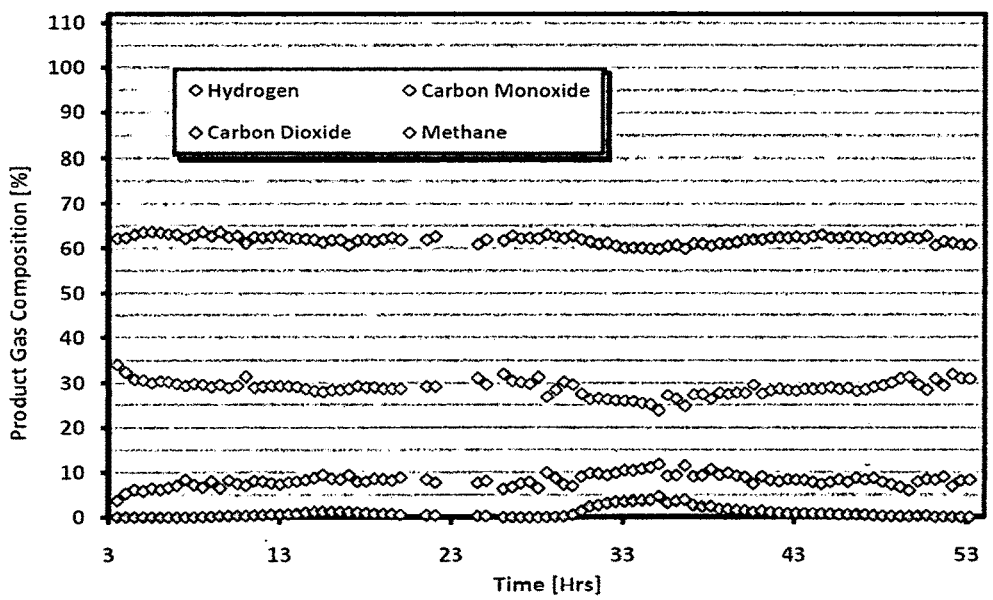
FIG. 4 shows a graph related to a catalyst that was found to be stable with lower water content in the feed (at <2.0/1.0 $H_2O/CH_4$) as demonstrated in a test with $CO_2/CH_4/H_2O$ (0.6/1.0/1.4) at 900° C.

The catalyst was found to be stable with lower water content in the feed (at <2.0/1.0 $H_2O/CH_4$) as demonstrated in a test with $CO_2/CH_4/H_2O$ (0.6/1.0/1.4) at 900° C. (Test D). Stable catalyst performance was achieved as shown in FIG. 4.

Figure 5:
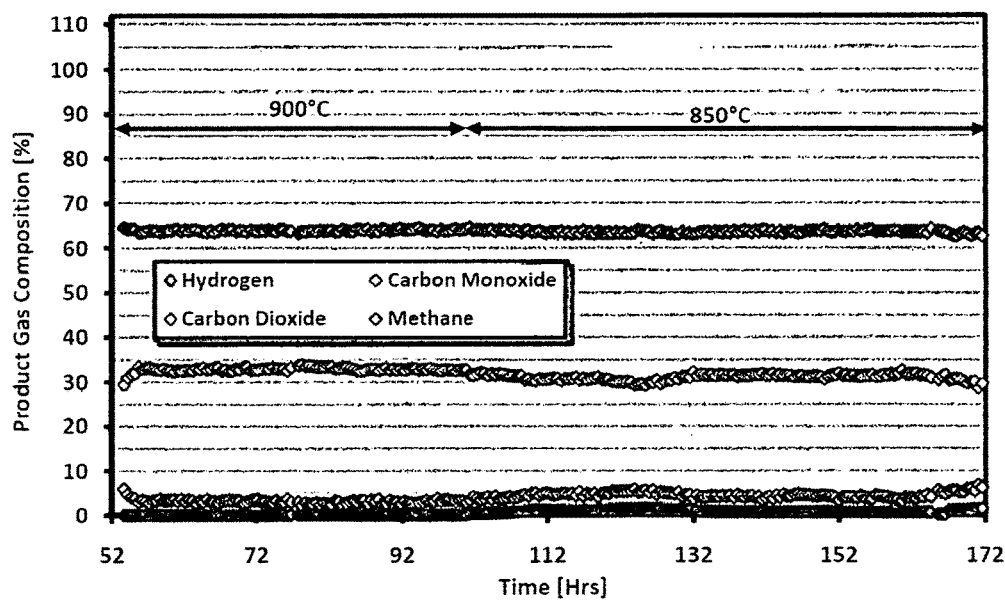
FIG. 5 shows a graph related to a catalyst tested at 900° C. and 10,400 $hr^{-1}$ (7,800 cc/g-hr) at 850° C. using a gas composition of $CO_2/CH_4/H_2O$ (0.4/1.0/0.93).

In the next set of test conditions using a gas composition of $CO_2/CH_4/H_2O$ (0.4/1.0/0.93), the catalyst was tested at 900° C. and 10,400 $hr^{-1}$ (7,800 cc/g-hr) at 850° C. (see FIG. 5).

Figure 6:
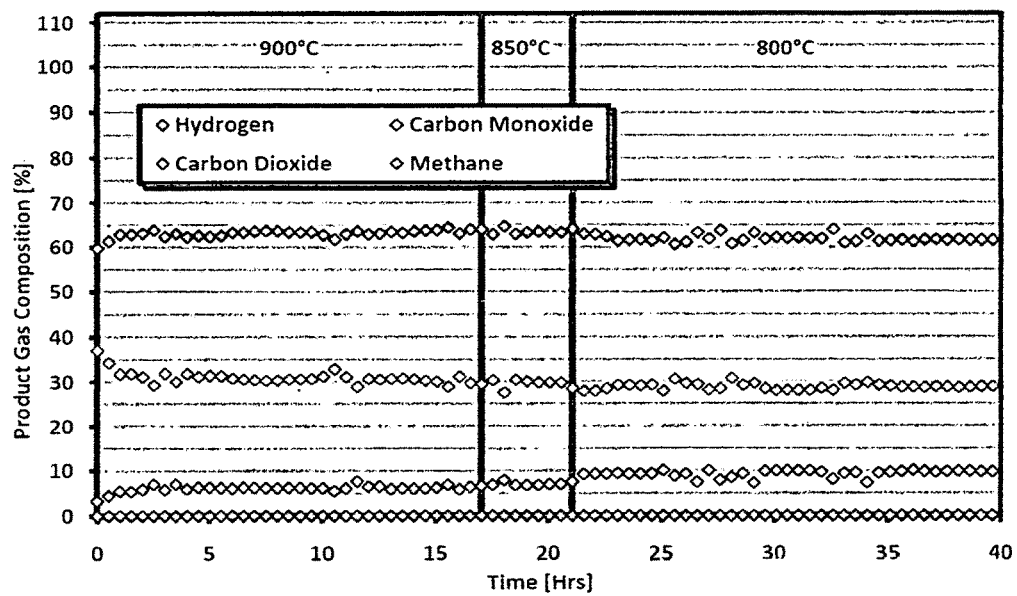
FIG. 6 shows a graph related to a catalyst that was stable when operating with a gas composition of $CO_2/CH_4/H_2O$ (0.6/1.0/1.4) from 800°-900° C.

As shown in FIG. 6 (test F), the catalyst was stable when operating with a gas composition of $CO_2/CH_4/H_2O$ (0.6/1.0/1.4) from 800-900° C.

Figure 7:
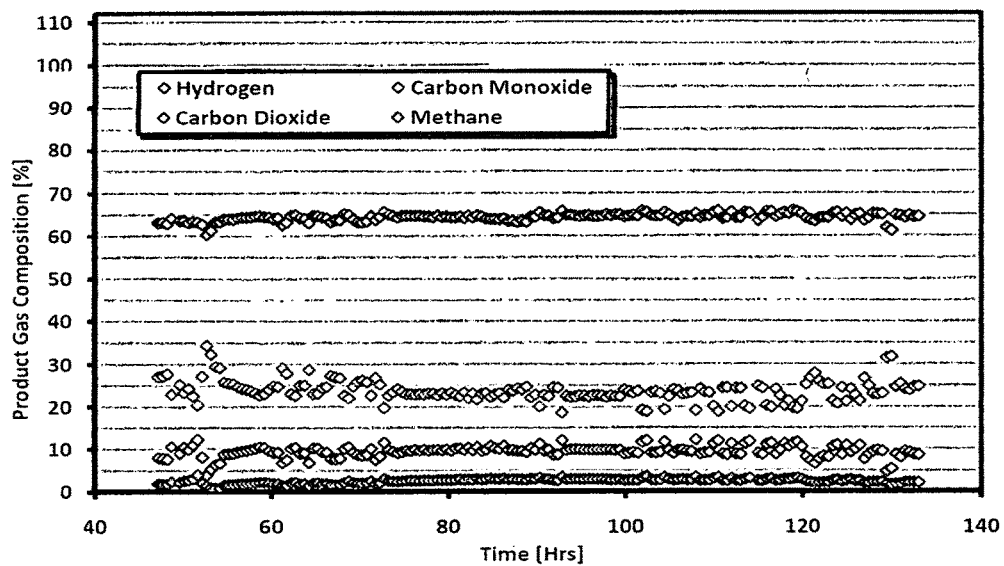
FIG. 7 shows a graph related to a catalyst tested with a gas composition of $CO_2/CH_4/H_2O$ (0.6/1.0/1.4) at 800° C.

Additional testing was carried out with the same gas composition of $CO_2/CH_4/H_2O$ (0.6/1.0/1.4) at 800° C. (see FIG. 7, Test G). Post-testing Temperature Programmed Oxidation (TPO) and optical analysis did not show any signs of carbon deposition.

In conclusion, it was found that a combination of steam methane and dry reforming (including the reactants $CO_2$, $CH_4$, and $H_2O$) produce a syngas with a $H_2/CO$ ratio of 1.8-2.0 that is ideal for subsequent liquid fuel production. Typically a $H_2O/CO_2$ ratio of 2.0-1.0 would be targeted in order to produce syngas in this ratio.

Example #3

The capability of the catalyst to tri-reform $CO_2$, $CH_4$, $H_2O$ & $O_2$ is presented in this example. Tri-reforming is typically defined as a combination of endothermic $CO_2$ (or Dry) reforming (Eq. 3) and steam reforming (Eq. 4) with exothermic oxidation of methane (Equations 5, 6, 7 described above).

Tri-reforming utilizes a single catalyst and the reactions outlined above occur in a single catalytic reactor system. This combination of reactions produces syngas with a $H_2/CO$ ratio in the proper range for subsequent diesel fuel production. Note again that oxygen is not required for achieving the appropriate syngas ratio and for stable operation of the catalyst, however since oxygen is available at in some flue gas applications and operation with some oxygen in the feed stream can allow for the flue gas to be used directly without separation.

When tri-reforming is used, oxygen levels should be kept under 6% of the total feed gas. Higher oxygen levels start to negatively affect $CO_2$ conversion. This fact has been recognized by several groups and this is one of the reasons that under auto-thermal reforming (ATR), $CO_2$ conversion is poor even at elevated temperatures.

Figure 8:
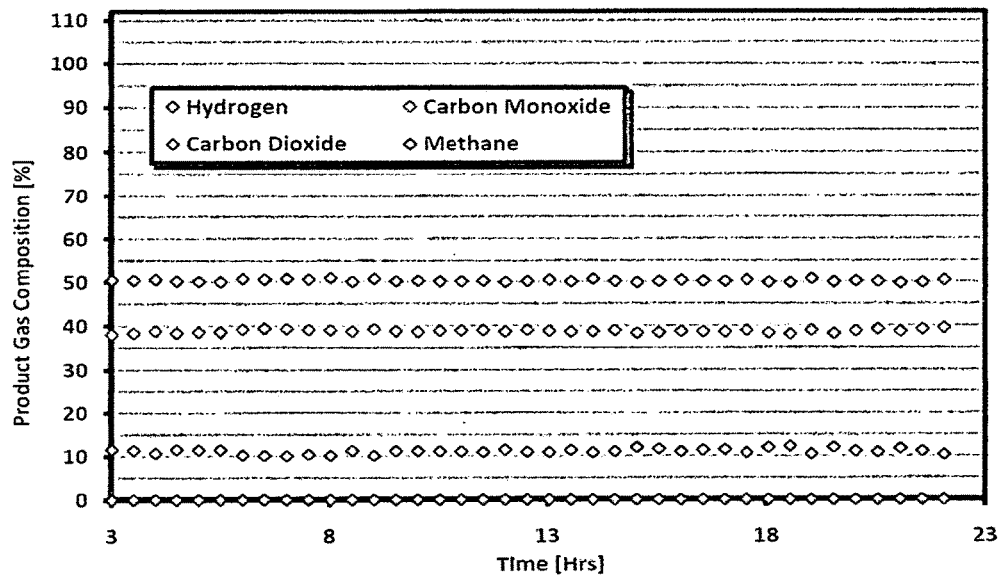
FIG. 8 shows a graph related to a tri-reforming test conducted at $CH_4$ (1.0)/$CO_2$ (1.0)/$H_2O$ (1.0)/$O_2$ (0.1) at 900° C. at 13,333 $hr^{-1}$ (10,000 cc/g-hr).

In the first test, reforming was conducted at $CH_4$ (1.0)/$CO_2$ (1.0)/$H_2O$ (1.0)/$H_2O$ (0.1) at 900° C. at 13,333 $hr^{-1}$ (10,000 cc/g-hr) and the data for tri-reforming test H is shown in FIG. 8.

Figure 9:
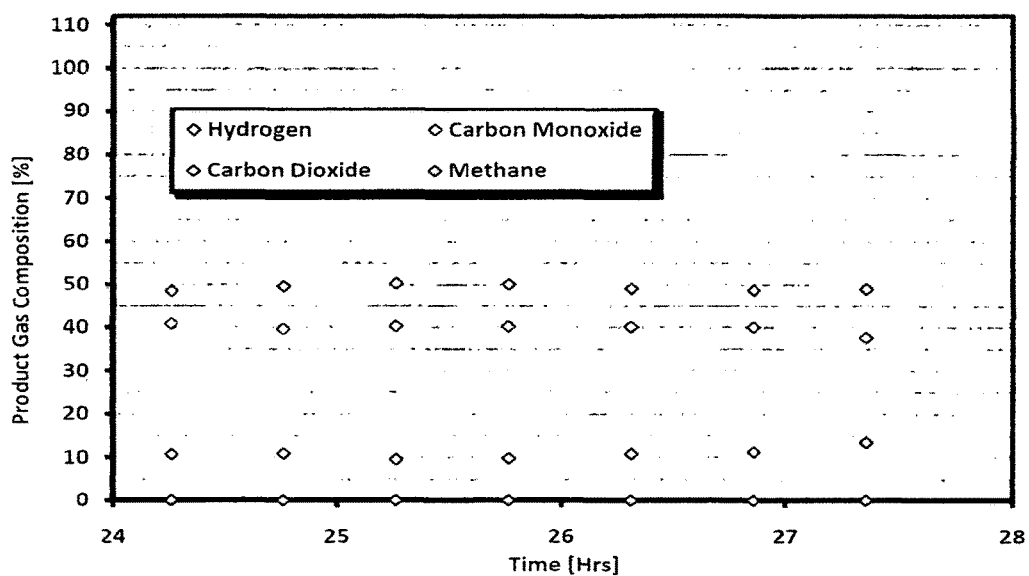
FIG. 9 shows a graph related to testing conducted at a feed gas composition $CH_4$ (1.0)/$CO_2$ (1.0)/$H_2O$ (1.0)/$O_2$ (0.05) at 900° C. and 16,000 $hr^{-1}$ (12,000 cc/g-hr).

FIG. 9 shows the results for Test I at a feed gas composition $CH_4$ (1.0)/$CO_2$ (1.0)/$H_2O$ (1.0)/$O_2$ (0.05) at 900° C. and 16,000 $hr^{-1}$ (12,000 cc/g-hr).

Figure 10:
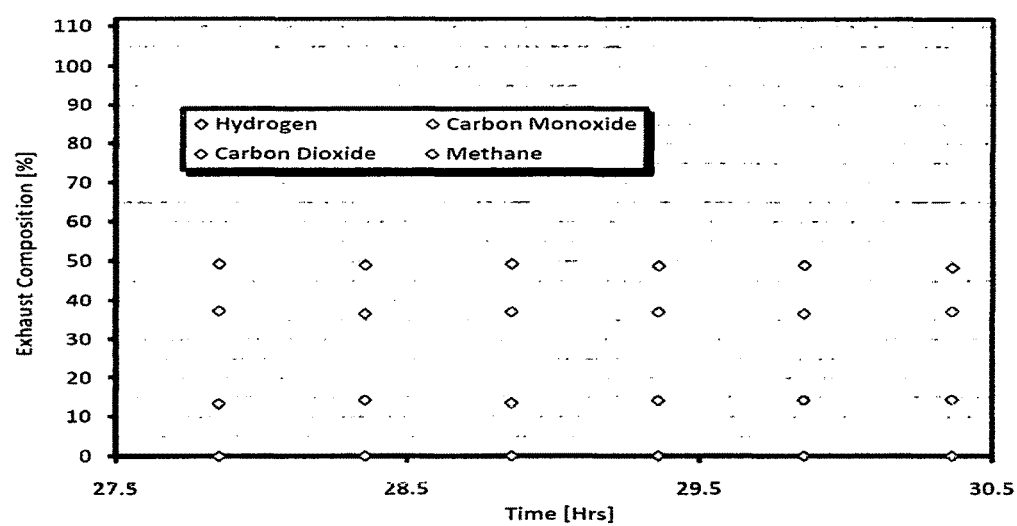
FIG. 10 shows a graph related to a test conducted with a feed gas composition of $CH_4$ (1.0)/$CO_2$ (1.0)/$H_2O$ (1.0)/$O_2$ (0.2) at 900° C. and 17,333 $hr^{-1}$ (13,000 cc/g-hr).
Figure 11:
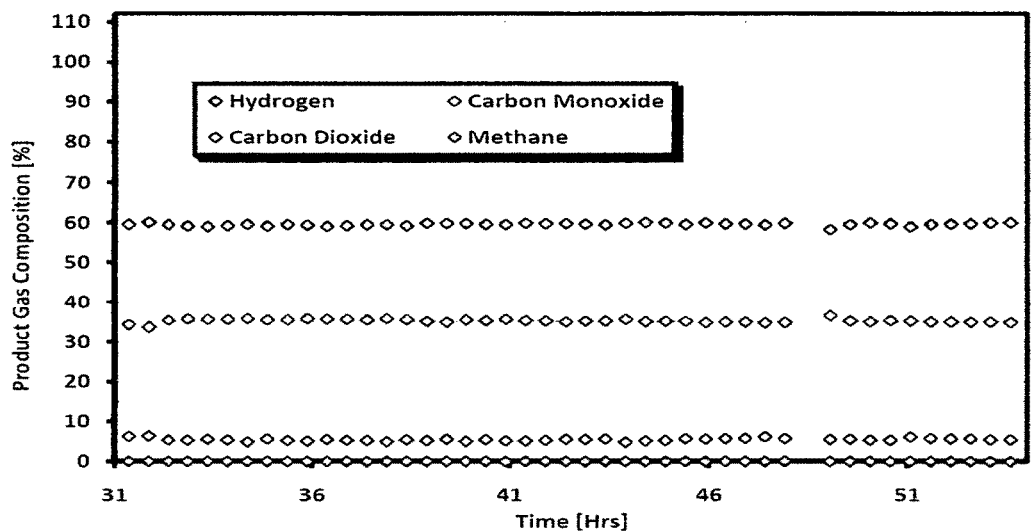
FIG. 11 shows a graph related to a tri-reforming test.

FIG. 10 shows results (test J) for a feed gas composition of $CH_4$ (1.0)/$CO_2$ (1.0)/$H_2O$ (1.0)/$O_2$ (0.2) at 900° C. and 17,333 $hr^{-1}$ (13,000 cc/g-hr) (Oxygen levels were 200% of Tri-reforming Test H).

Figure 12:
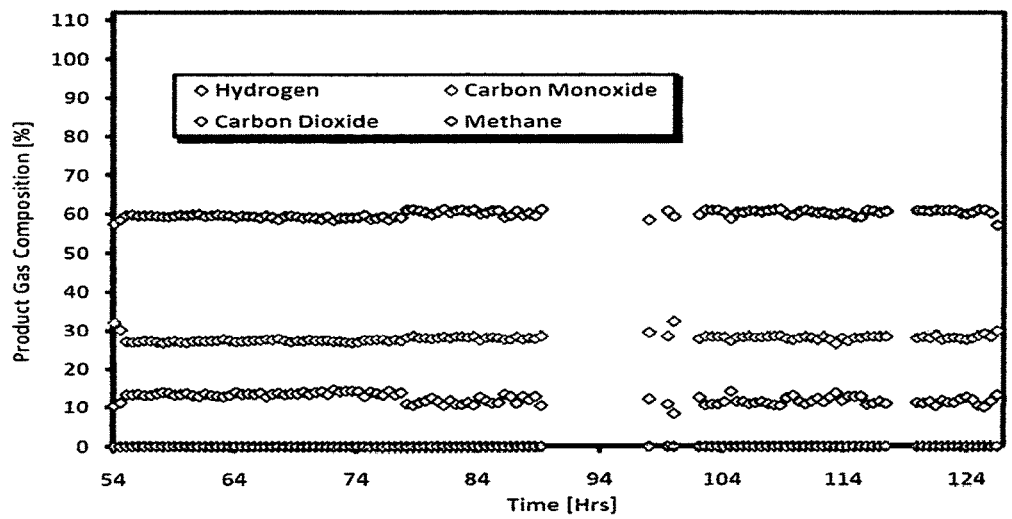
FIG. 12 shows a graph related to a test where the $CO_2$ ratio was increased to 0.6, the steam ratio was increased to 1.7, and $O_2$ increased to 0.2. Gas hourly space velocity was 18,666 $hr^{-1}$ (14,000 cc/g hr).

In the next test (E), the $CO_2$ ratio was increased to 0.6, the steam ratio was increased to 1.7, and $O_2$ increased to 0.2. Gas hourly space velocity was 18,666 $hr^{-1}$ (14,000 cc/g hr) as shown in FIG. 12 (Test L).

Figure 13:
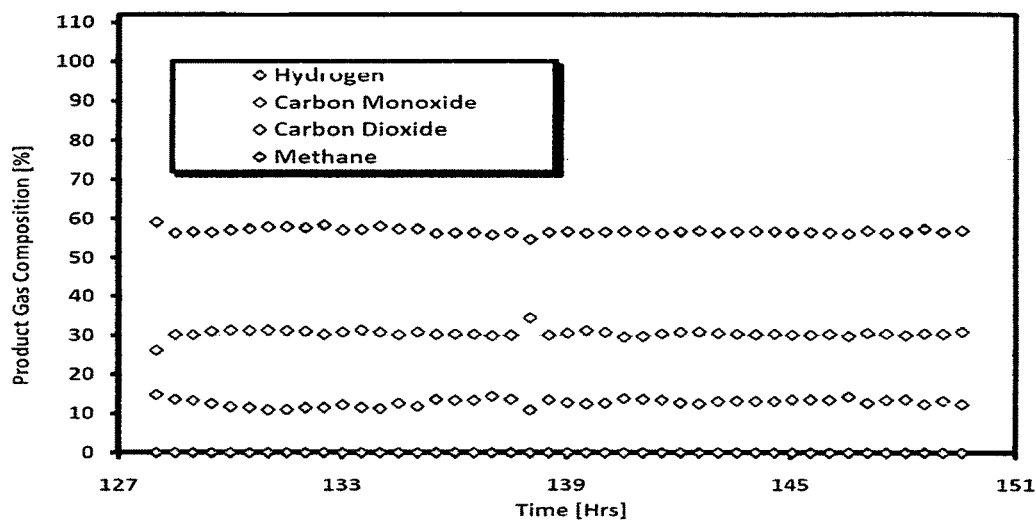
FIG. 13 shows a graph related to a test where the carbon dioxide ratio was increased to 0.8, the steam to methane ratio was varied between 1.7 and 1.35, while keeping $O_2$ at 0.1 (GHSV =16,333 $hr^{-1}$ or 12,250 cc/g hr).
Figure 14:
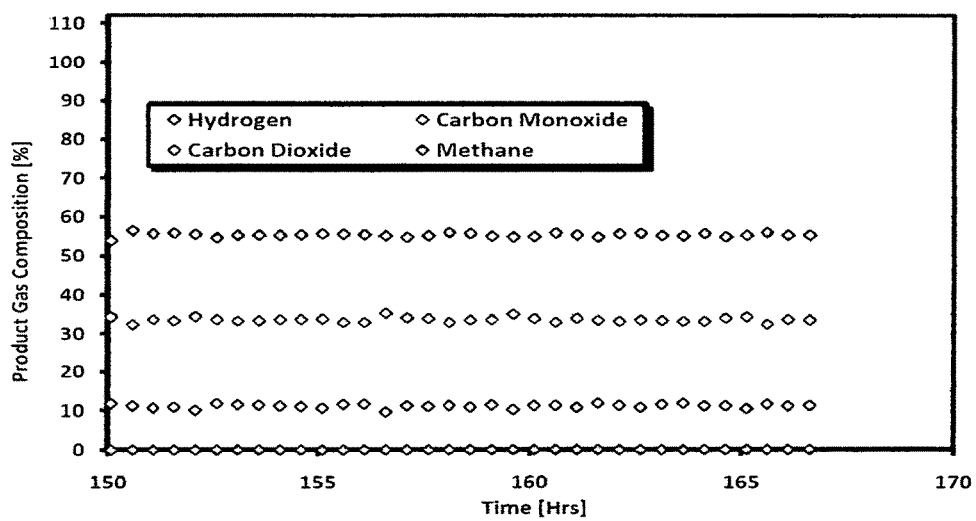
FIG. 14 shows a graph related to a test where the carbon dioxide ratio was increased to 0.8, the steam to methane ratio was varied between 1.7 and 1.35, while keeping $O_2$ at 0.1 (GHSV =18,000 $hr^{-1}$ or 13,500 cc/g hr).

Under the final two conditions, the carbon dioxide ratio was increased to 0.8, the steam to methane ratio was varied between 1.7 and 1.35, while keeping $O_2$ at 0.1. The results of these tests are shown in FIG. 13 (GHSV=16,333 $hr^{-1}$ or 12,250 cc/g hr) and FIG. 14 (GHSV=18,000 $hr^{-1}$ or 13,500 cc/g hr). Both tests were stable during the 20 hours of testing at 900° C. for each condition. Decreasing the steam in the feed improves carbon dioxide conversion. Overall, the catalyst was very stable for all of the tri-reforming conditions examined. No carbon formation or deactivation of the catalyst was observed.

In conclusion, tri-reforming was found to provide high gas hourly space velocities (GHSV), stable catalyst performance, and the proper $H_2/CO$ ratio (~2.0) for subsequent conversion to diesel fuel or chemicals.

The invention claimed is:

1. A nickel-based, solid solution catalyst for producing syngas, wherein the solid solution catalyst is not coated on a substrate, and wherein the catalyst is in contact with $CO_2$, $CH_4$ and $H_2O$, and wherein the catalyst is capable of producing syngas with a pre-selected ratio of $H_2/CO$, and wherein the $H_2/CO$ ratio is capable of being varied based on the production process used to produce the syngas, wherein the nickel-based, solid solution catalyst comprises only one transition metal, and wherein the transition metal is nickel.

2. The nickel-based, solid solution catalyst according to claim 1, wherein the nickel-based, solid solution catalyst is stable up to 1,100° C.

3. The nickel-based, solid solution catalyst according to claim 1, wherein the nickel-based, solid solution catalyst does not include a precious metal.

4. The nickel-based, solid solution catalyst according to claim 1, wherein the catalyst formulation is capable of producing syngas with a $H_2/CO$ ratio ranging from 1.5 to 2.5.

5. The nickel-based, solid solution catalyst according to claim 1, wherein the catalyst formulation is capable of producing syngas with a $H_2/CO$ ratio ranging from 0.7 to 1.0.

6. A nickel-based, solid solution catalyst for producing syngas, wherein the solid solution catalyst is not coated on a substrate, and wherein the catalyst is in contact with $CO_2$, $CH_4$, $H_2O$ and $O_2$, and wherein the catalyst is capable of producing syngas with a pre-selected ratio of $H_2/CO$, and wherein the $H_2/CO$ ratio is capable of being varied based on the production process used to produce the syngas, wherein the nickel-based, solid solution catalyst comprises only one transition metal, and wherein the transition metal is nickel.

7. The nickel-based, solid solution catalyst according to claim 6, wherein the nickel-based, solid solution catalyst is stable up to 1,100° C.

8. The nickel-based, solid solution catalyst according to claim 6, wherein the nickel-based, solid solution catalyst does not include a precious metal.

9. The nickel-based, solid solution catalyst according to claim 6, wherein the catalyst formulation is capable of producing syngas with a $H_2/CO$ ratio ranging from 1.5 to 2.5.

10. The nickel-based, solid solution catalyst according to claim 6, wherein the catalyst formulation is capable of producing syngas with a $H_2/CO$ ratio ranging from 0.7 to 1.0.

* * * * *